United States Patent
Schwaibold

(10) Patent No.: US 11,159,619 B2
(45) Date of Patent: Oct. 26, 2021

(54) SYSTEM FOR DATA TRANSFER

(71) Applicant: Loewenstein Medical Technology S.A., Luxembourg (LU)

(72) Inventor: Matthias Schwaibold, Karlsruhe (DE)

(73) Assignee: LOEWENSTEIN MEDICAL TECHNOLOGY S.A., Luxembourg (LU)

( * ) Notice: Subject to any disclaimer, the term of this patent is extended or adjusted under 35 U.S.C. 154(b) by 159 days.

(21) Appl. No.: 16/380,782

(22) Filed: Apr. 10, 2019

(65) Prior Publication Data

US 2019/0320024 A1    Oct. 17, 2019

(30) Foreign Application Priority Data

Apr. 12, 2018 (DE) .................. 102018002997.3

(51) Int. Cl.
| | |
|---|---|
| H04L 29/08 | (2006.01) |
| H04W 4/30 | (2018.01) |
| A61M 16/06 | (2006.01) |
| G06F 9/54 | (2006.01) |

(52) U.S. Cl.
CPC ............ *H04L 67/12* (2013.01); *A61M 16/06* (2013.01); *G06F 9/542* (2013.01); *H04W 4/30* (2018.02); *A61M 2205/3553* (2013.01); *A61M 2205/3584* (2013.01); *A61M 2205/50* (2013.01)

(58) Field of Classification Search
CPC ......... H04L 67/12; H04W 4/30; A61M 16/06; A61M 2205/3553; A61M 2205/3584; A61M 2205/50; G06F 9/542

USPC ....................................................... 709/203
See application file for complete search history.

(56) References Cited

U.S. PATENT DOCUMENTS

| | | | |
|---|---|---|---|
| 5,291,938 A | 3/1994 | Metevelis et al. | |
| 5,950,621 A | 9/1999 | Klockseth | |
| 2008/0271010 A1 | 10/2008 | Scholler | |
| 2009/0081951 A1* | 3/2009 | Erdmann | G06F 19/3418 455/41.2 |

(Continued)

FOREIGN PATENT DOCUMENTS

| | | | | |
|---|---|---|---|---|
| DE | 102015008946 A1 | 3/2016 | | |
| EP | 1478164 B1 * | 8/2011 | ............ | G04R 20/00 |

(Continued)

OTHER PUBLICATIONS

Rehm, Development of a research-oriented system for collecting mechanical ventilator waveform data, Oct. 28, 2017, Journal of the American Medical Informatics Association, https://academic.oup.com/jamia/article/25/3/295/4571786 (Year: 2017).*

(Continued)

*Primary Examiner* — Zi Ye
(74) *Attorney, Agent, or Firm* — Abel Schillinger, LLP

(57) ABSTRACT

The present invention relates to a system for data transfer between a server and a respirator which comprises a source for breathing gas, and at least one interface to enable a data transfer, a device for determining data, a control unit, a memory, and a timer unit for specifying a system time. The respirator is configured to give the data a timestamp, to store them and to transfer them at a later point in time. The timestamp is designed so that it cannot be adjusted, or can only be adjusted to a limited extent to a tolerance window.

20 Claims, 2 Drawing Sheets

(56) References Cited

U.S. PATENT DOCUMENTS

| | | |
|---|---|---|
| 2009/0163793 A1 | 6/2009 | Koehler |
| 2011/0249006 A1* | 10/2011 | Wallace ............... G06F 3/0482 345/440 |
| 2012/0310669 A1 | 12/2012 | Carlberg |
| 2014/0000609 A1 | 1/2014 | Steinhauer |
| 2014/0276048 A1* | 9/2014 | Kiley .................. A61B 8/4236 600/438 |
| 2016/0058962 A1 | 3/2016 | Bychkov |

FOREIGN PATENT DOCUMENTS

| | | |
|---|---|---|
| EP | 2392253 A1 | 12/2011 |
| WO | 2007030457 A1 | 3/2007 |
| WO | WO-2015171487 A1 * | 11/2015 ............. G06F 21/55 |

OTHER PUBLICATIONS

ISiek, How to prevent Domain users from changing Time and Date, Nov. 6, 2011, social.technet.microsoft.com, https://social.technet.microsoft.com/Forums/ie/en-US/c5d8775b-3827-4491-9f8b-0876231ff6c0/how-to-prevent-domain-users-from-changing-time-and-date?forum=winserverGP (Year: 2011).*

CareFusion, AVEA Ventilator Systems Operator's Manual, 2006-2017, vyaire.com, https://www.vyaire.com/sites/default/files/2020-03/manual-avea-operators-rev-w-I2786-w.pdf (Year: 2006).*

* cited by examiner

SYSTEM FOR DATA TRANSFER

CROSS-REFERENCE TO RELATED APPLICATIONS

The present application claims priority under 35 U.S.C. § 119 of German Patent Application No. 102018002997.3 filed on Apr. 12, 2018, the entire disclosure of which is expressly incorporated by reference herein.

BACKGROUND OF THE INVENTION

1. Field of the Invention

The present invention relates to a system for data transfer between a server and a respirator.

2. Discussion of Background Information

Therapy with respirators is known in the prior art, and respirators increasingly comprise digital interfaces for data exchange. The respirators generally comprise at least one interface to enable a data transfer. For the purpose of data exchange, the respirators are often fitted with an interface for data exchange with a network. It is conventional in the prior art that such an interface can be implemented in a wired form, for example as an RJ45 data interface, or wirelessly, for example as a WLAN, mobile radio, IoT, M2M or Bluetooth interface.

A large amount of data can be exchanged over such a data interface. The software of the respirator can, for example, be updated by means of an update through access to remote data, as described in DE 10 2015 008 946 A1, the entire disclosure of which is incorporated by reference herein.

Treatment data, such as settings, measured values of therapeutic or physiological parameters, or also patient data, can furthermore be transmitted to a remote device, for example to a server, for storing and making available to third parties, as described in EP 2 392 253 A1, the entire disclosure of which is incorporated by reference herein.

The solutions known from the prior art however have the disadvantage that data, in particular patient data, that are required for a further analysis, can be incorrectly assigned in the event of a system error, for example a wrongly set clock time such as can result when changing between summer and winter time. Data can, for example, be displayed as if collected on a different day. This causes significant problems when assigning the data during the transfer.

When, in particular, the data are not transferred in real time, but are to be transferred at a later point in time, an incorrect clock time can have the results that the transferred data cannot be assigned and are thus unusable.

In view of the foregoing, it would be advantageous to have available a system for data transfer that ensures that the collected data can be correctly stored and assigned.

This object is achieved by a system for data transfer in accordance with claim 1 of the invention.

SUMMARY OF THE INVENTION

The present invention provides a system for data transfer between a server and a respirator wherein the respirator comprises a source for breathing gas and at least one interface to enable a data transfer, a device for determining data, a control unit, a memory, and a timer unit for specifying a system time. The data transfer can, for example, comprise a transfer of daily statistical values that are transferred as one unit at the end of the day. If the transfer is disrupted, the daily statistical values are stored and are transferred coherently on another day. Alternatively, a data transfer can be carried out by means of an application. A further alternative is the exchange of data between diagnostic devices.

According to the invention, the respirator is configured to give the data a timestamp, to store them and to transfer them at a later point in time, wherein the timestamp is designed so that it cannot be adjusted, or can only be adjusted to a limited extent to a tolerance window. This offers the advantage that it is possible to establish on what date and at what time the data were recorded or the therapy was performed. It is also possible to ensure that the date and the clock time in the respirator are sufficiently correct without them being manually adjustable. "At a later point in time" means that the respirator is designed not to transfer the data in real time, but to store them temporarily in a memory and to transfer them at a later point in time. The timestamp is specified as a rule by an external time provision service, for example a time server. The respirator is typically configured to communicate at least once with the time provision service. The generated timestamp is stored with the respective date on the respirator, and transmitted together with the data during a transfer.

In a development of the invention, the system is designed to carry out a comparison of a system time of the respirator with a server time of the server on the basis of the timestamp when the data transfer is started. A data transfer is also referred to as telemonitoring. The system time is defined by means of the timestamp. The server time is defined by the server. As a data transfer/telemonitoring is beginning, the system is designed to communicate the timestamp or the system time of the respirator to the server.

In a further development, the respirator is designed to receive a system time from the server and to adjust the system time automatically. This has the advantage that the correct time is set automatically.

In one embodiment, the server is designed to assess a difference between the system time and the server time, and to convey a corresponding assessment to the respirator. The server is designed to receive the data transmitted from the respirator, in particular the timestamp or the system time. The server is designed to compare the system time with the server time and to establish a difference. Optionally, the server can be designed to maintain a tolerance window within which differing times (system time from server time) are tolerated and are deemed by the server to be correct. Such a tolerance window can, for example, be between 0.1 seconds up to 1 minute.

In a further development according to the invention, the respirator is designed to perform a login of the respirator at the server on the basis of the assessment of the system time by the server. The respirator can here decline a registration depending on the assessment of the system time. The server is designed to transmit the assessment to the respirator. On the basis of the assessment transmitted by the server, the respirator is designed to carry out a login of the respirator at the server for data transfer. If the assessment of the server finds that the system time differs or is outside the tolerance window, the respirator is designed to decline a login at the server for data transfer. If the system time of the respirator is within the tolerance window, or if it does not differ from the server time, the respirator is designed to permit a login at the server for data transfer.

In a further development of the invention the system time is again manually set by a user, wherein the server controls the respirator to prompt the user to specify the system time, so that a defined agreement with the server time is achieved. A prompt to specify the system time is, for example, given to the user if the system time is outside the tolerance window or differs from the server time.

In a further development of the invention, the respirator is designed, on the basis of the assessment of the system time by the server, to request a system time correction from a user in order to perform the login at the server. Only after the new system time has been manually specified by the user and a renewed assessment of the system time by the server, and an agreement between the system time and the server time, can a login of the respirator take place at the server.

In one embodiment, the system is designed to prevent an adjustment of the system time by the user when the respirator has already once successfully logged in. This offers the advantage that the system time cannot be accidentally/deliberately altered by a user. As a rule, however, the system time can be adjusted on a test bed or via a service access at the device. As a rule, the system time cannot be set back to before the end of the last stored therapy.

In a further embodiment, the respirator is designed to transmit the data and the system time to the server via the interface. The respirator is usually designed to comprise an interface that is suitable for data transfer.

In a further embodiment of the invention the data and the system time are transferred from the respirator and stored in a server memory if there is defined agreement between the server time and the system time. Through the transfer of the data and system time from the respirator, the memory space that these data have occupied on the respirator is again released.

In a further development of the invention, the respirator receives a timestamp from a time server at least at certain times. As a rule the respirator is designed to carry out a time comparison of its system time with a server time of a time server at least once a day. Other comparison intervals can, alternatively, be set. A comparison can, for example, take place weekly.

In a further development, the time server makes the timestamp available over the Internet or a mobile telephony network or a local wireless network (Wi-Fi, Bluetooth), or is a PC or a time clock or a device. This offers the advantage that a best possible access of the respirator to a server is enabled according to local conditions.

In a development according to the invention, the respirator, alternatively or in addition to the timer unit, comprises an internal counter that continuously generates new counter states which are stored together with the data, wherein the current counter state is conveyed to the server with every data transfer. By conveying the current counter state with each data transfer, the server, which knows the current server time, can in this way determine an association between the counter state and the date.

In a further development the server compares the current counter state with the server time, and performs an association between the counter state and the server time, and assigns the data, and thereby the old counter states that are assigned to the data, also chronologically corresponding to the server time. This makes it possible to compare the internal counter state with the server time.

The present invention further provides a system for data transfer between a server and a respirator wherein the respirator comprises a source for breathing gas and at least one interface to enable a data transfer, a device for determining data, a control unit, a memory, and a timer unit for specifying a system time.

According to the invention, the respirator at least sometimes places the data in the memory and assigns the system time as a timestamp to the data, wherein the system time is transmitted via the interface to the server, wherein the server comprises a server timer unit for the provision of a server time and a comparison apparatus, wherein the comparison apparatus compares the server time with the system time and in the event of a defined agreement between the server time and the system time transmits the data from the respirator and places them in the server memory, and wherein the respirator, in the event of a defined deviation between the server time and the system time prevents the transfer of data from the respirator until the system time is newly specified in such a way that a defined agreement with the server time is achieved, wherein the newly specified system time is applied to the timestamp in the memory of the respirator in such a way that a new timestamp is assigned to the data, whereupon the data is transferred to the server with the new timestamp. This offers the advantage that data, for example patient data, is given a correct timestamp during a telemonitoring/a data transfer, and can thereby be correctly assigned during the further processing. As a rule, data that have already been stored retain their timestamp, and data generated in the future are given a new timestamp according to the new date. The system can optionally prescribe a tolerance window within which a deviating system time is assessed as correct. A tolerance window can, for example, be between 0.1 seconds and 1 minute. In the presence of the deviation, the user is typically prompted to set the system time before it is possible to begin a data transfer.

The present invention further provides a system for data transfer between a server and a respirator wherein the respirator comprises a source for breathing gas and at least one interface to enable a data transfer, a device for determining data, a control unit, a memory, and a timer unit for specifying a system time.

According to the invention the respirator is designed to give the data a timestamp, to store them and to transfer them at a later point in time, wherein the timestamp is designed such that it cannot be adjusted, or only adjusted to a limited extent to a tolerance window, wherein the system is designed to carry out a comparison of a system time of the respirator with a server time of the server on the basis of the timestamp when the data transfer is started, wherein the system time is manually adjustable before the respirator is logged in to the server, wherein the server is designed to assess the manually adjusted system time before a login at the server and to compare it with the server time. The server is designed to check the system time through comparison with the server time at the first login. If the system time deviates from the tolerance window, the user is forced to correct the time before logging in at the server.

The present invention further provides a system for data transfer between a server and a respirator wherein the respirator comprises a source for breathing gas and at least one interface to enable a data transfer, a device for determining data, a control unit, a memory, and a timer unit for specifying a system time.

According to the invention the respirator is designed to give the data a timestamp, to store them and to transfer them at a later point in time, wherein the timestamp is designed such that it cannot be adjusted, or only adjusted to a limited extent to a tolerance window, wherein the system is designed to carry out a comparison of a system time of the respirator with a server time of the server on the basis of the timestamp when the data transfer is started, wherein the respirator comprises a display time that is designed to differentiate itself from the system time by up to 24 hours. In this way the user is able to receive a display of the correct local time (time zone) on a display of the respirator, and to change between winter and summer time. As a rule the system time is stored with the stored data as the timestamp. The display time (or a difference between the display time and the system time) can optionally be stored, so that when examining and evaluating the data, the information relating to the local time of the user/patient can also be examined.

BRIEF DESCRIPTION OF THE DRAWINGS

Preferred exemplary embodiments of the invention are explained in more detail below with reference to highly simplified schematic illustrations. Here.

The same design elements are each given the same reference numerals in the figures.

DETAILED DESCRIPTION OF EXEMPLARY EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
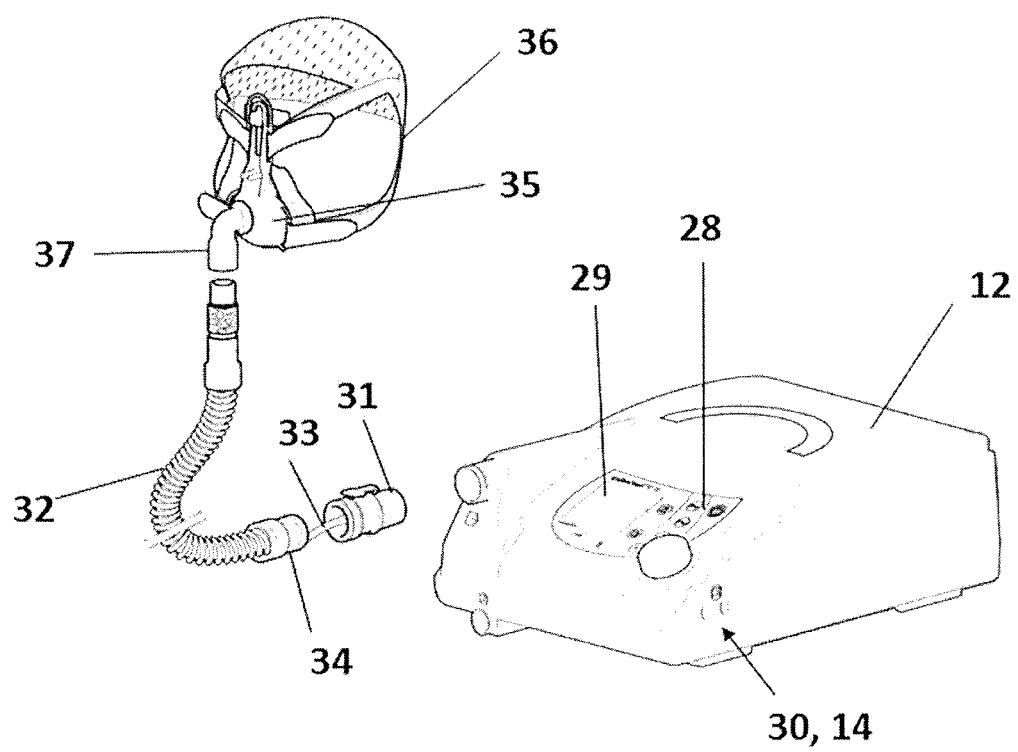
FIG. 1 shows a basic structure of a respirator.

FIG. 1 shows the basic structure of a respirator 12. A breathing gas pump is arranged in the interior of the device in the region of a device housing with operating panel 28 and display 29. A connecting hose 32 is connected via a coupling 31. An additional pressure measuring hose 33, which can be connected to the device housing via a pressure inlet nozzle 34, can run along the connecting hose 32. The device housing 12 comprises at least one interface 30, 14 to enable a data transfer. A humidifier can be fitted by means of an adapter.

An exhalation element is arranged in the region of an extension of the connecting hose 32 that faces away from the device housing 12. An exhalation valve can also be used.

FIG. 1 furthermore shows a patient interface 35 formed as a breathing mask 10 which is realized here by way of example as a nasal mask. A fixing in the region of a head of a patient can take place by means of headgear 36. The patient interface 35 comprises a coupling element 37 in the region of its extension that faces toward the connecting hose 32.

The input and/or output of data such as, for example, dead space volume, can take place via the interface 30, 14. The interfaces 14, 30 can be realized in wired form, as an infra-red interface, as a Bluetooth interface, a mobile telephony interface, an IoT or M2M interface, or as USB.

The respirator 12 according to the invention is designed so that it can be connected to a patient via a hose and a patient interface 10 in order to provide respiration. It comprises a source for breathing gas which is, for example, designed as an electric motor with a fan wheel, and an apparatus for determining pressure and/or flow and/or volume of the breathing gas, as well as a control unit which is designed such that for each breathing cycle it determines a breathing gas pressure on the basis of a predetermined value for the patient and/or on the basis of measurement signals for the parameters of pressure and/or flow and/or volume, and regulates the source for breathing gas such that the breathing gas pressure is generated.

The respirator 10 has a memory for storing data that represents the period of usage and the therapy quality and, in addition, the function/servicing of the device.

The control unit is, furthermore, designed such that it determines the current pressure and/or flow and/or the volume of breathing gas, and represents the current value via a display connected to the control unit. The control unit is, moreover, designed such that it determines trend changes in its calculations of one or more parameters over time, wherein the trend changes can be displayed on the display.

Recorded data can also be transferred via a modem or another interface 30, 14.

The respirator 12 shown in FIG. 1 is suitable for use in a system 10 for data transfer according to the invention.

Figure 2:
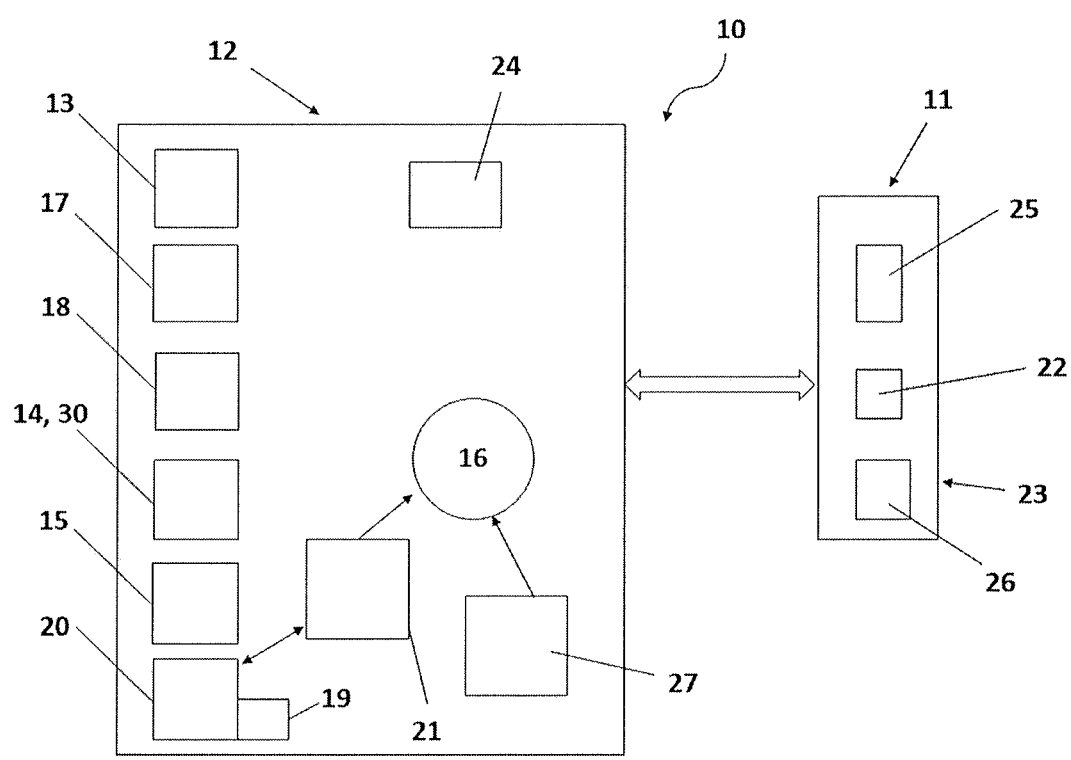
FIG. 2 shows a schematic illustration of the system for data transfer according to the invention.

FIG. 2 shows a schematic illustration of the system 10 for data transfer according to the invention. The system according to the invention comprises the server 11 as well as the respirator 12. The respirator 12 comprises at least one source for breathing gas 13, at least one interface 14, 30 to enable a data transfer, a device 15 for determining data 16, a control unit 17, a memory 18 and a timer unit 19 for specifying a system time 20. The respirator 12 assigns the system time 20 to the data 16 as a timestamp, and places the captured data in a memory 18. As a rule the system time 20 or the data 16 with the timestamp 21 are conveyed via the interface 20 to the server 11.

The server 11 comprises a server timer unit 25 for the provision of a server time 22 and a comparison apparatus 26. The comparison apparatus 26 compares the server time 22 to the system time 20 and in the event of a defined agreement between the server time 22 and the system time 20 transfers the data 16 from the respirator 12 and places it in the server memory.

If a deviation between the server time 22 and the system time 20 occurs, the respirator 10 prevents the transfer of data 16 from the respirator 10 until the system time 20 that achieves a defined agreement with the server time 22 is again specified. The respirator 10 can set up a tolerance window, within whose range a difference between the system time 20 and the server time 22 will be tolerated by the respirator 10. In the presence of a deviation of the system time 20 from the server time 22, the respirator 10 will output a prompt to a user 38 of the respirator 10 to set the system time 20.

The newly specified system time 20 is applied to the timestamp 21 in the memory 18 of the respirator 10. A new timestamp 21 is here assigned to the respective data 16. The data 16, with the newly assigned timestamps 21, are transferred to the server 11 and assessed again. If there is an agreement between the new system time 20 and the server time 22, the respirator 10 is logged in to the server 11, and the data 16 are transferred to the server 11.

LIST OF REFERENCE NUMERALS

10 System
11 Server
12 Respirator
13 Source for breathing gas
14, 30 Interface

15 Device for determining data
16 Data
17 Control unit
18 Memory
19 Timer unit
20 System time
21 Timestamp
22 Server time
23 Time server
24 Internal counter
25 Server timer unit
26 Comparison apparatus
27 New timestamp
28 Control device
29 Display
30, 14 Interface
31 Coupling
32 Connecting hose
33 Pressure measuring hose
34 Pressure inlet nozzle
35 Patient interface
36 Headgear
37 Coupling element
38 User

What is claimed is:

1. A system for data transfer between a server and a respirator, wherein the respirator comprises a source for breathing gas, at least one interface to enable a data transfer, a device for determining data, a control unit, a memory, and a timer unit for specifying a system time, the respirator being configured to give the data a timestamp, to store the data and to transfer the data at a later point in time, the timestamp being designed so that it cannot be adjusted, or can only be adjusted to a limited extent to a tolerance window.

2. The system of claim 1, wherein the system is configured to carry out a comparison of a system time of the respirator with a server time of the server on the basis of the timestamp when the data transfer is started.

3. The system of claim 1, wherein the respirator is configured to receive a system time from the server and to adjust the system time automatically.

4. The system of claim 1, wherein the server is configured to assess a difference between system time and server time, and to convey a corresponding assessment to the respirator.

5. The system of claim 1, wherein the respirator is configured to perform a login of the respirator at the server on the basis of an assessment of a system time by the server.

6. The system of claim 1, wherein when a system time is again manually set by a user, the server controls the respirator to prompt the user to specify a system time, so that a defined agreement with a server time is achieved.

7. The system of claim 1, wherein the respirator is configured, on the basis of an assessment of a system time by the server, to request a system time correction from a user in order to perform a login at the server.

8. The system of claim 1, wherein the system is configured to prevent an adjustment of the system time by a user when the respirator has already successfully been logged in once.

9. The system of claim 1, wherein the respirator is configured to transmit the data and a system time via the interface to the server.

10. The system of claim 1, wherein when there is defined agreement between server time and system time, the data and the system time are transferred from the respirator and stored in a server memory.

11. The system of claim 1, wherein the respirator receives at least sometimes a timestamp from a time server.

12. The system of claim 11, wherein the time server provides the timestamp over the Internet, or a radio telephony network, or a local radio network (Wi-Fi, Bluetooth), or is a PC or a radio clock or a device.

13. The system of claim 1, wherein the respirator comprises, alternatively or in addition to the timer unit, an internal counter that continuously generates new counter states which are stored together with the data, the current counter state being conveyed to the server with every data transfer.

14. The system of claim 13, wherein the server compares the current counter state with a server time, and performs an association between the counter state and the server time, and assigns the data, and thereby old counter states that are assigned to the data, also chronologically corresponding to the server time.

15. The system of claim 1, wherein the system is configured to carry out a comparison of a system time of the respirator with a server time of the server on the basis of the timestamp when the data transfer is started, the respirator being configured to receive a system time from the server and to adjust the system time automatically.

16. The system of claim 1, wherein the system is configured to carry out a comparison of a system time of the respirator with a server time of the server on the basis of the timestamp when the data transfer is started, the respirator being configured to receive a system time from the server and to adjust the system time automatically, and the server being configured to assess a difference between the system time and the server time, and to convey a corresponding assessment to the respirator.

17. The system of claim 1, wherein the respirator is configured to receive a system time from the server and to adjust the system time automatically, the respirator being configured to perform a login of the respirator at the server on the basis of an assessment of the system time by the server.

18. The system of claim 1, wherein the respirator at least sometimes places the data in the memory and assigns a system time as a timestamp to the data, wherein the system time is transmitted via the interface to the server, wherein the server comprises a server timer unit for the provision of a server time and a comparison apparatus, wherein the comparison apparatus compares the server time with the system time and in the event of a defined agreement between server time and system time transmits the data from the respirator and places them in a server memory, and wherein the respirator, in the event of a defined deviation between server time and system time prevents the transfer of data from the respirator until the system time is newly specified in such a way that a defined agreement with the server time is achieved, the newly specified system time being applied to the timestamp in the memory of the respirator in such a way that a new timestamp is assigned to the data, whereupon the data is transferred to the server with the new timestamp.

19. A system for data transfer between a server and a respirator, wherein the respirator comprises a source for breathing gas, at least one interface to enable a data transfer, a device for determining data, a control unit, a memory, and a timer unit for specifying a system time, wherein the respirator is configured to give the data a timestamp, to store the data and to transfer the data at a later point in time, wherein the timestamp is designed so that it cannot be adjusted, or can only be adjusted to a limited extent to a tolerance window, wherein the system is configured to carry out a comparison of a system time of the respirator with a server time of the server on the basis of the timestamp when the data transfer is started, wherein the system time is manually adjustable before the respirator is logged into the server, and wherein the server is configured to assess a manually adjusted system time before a login at the server and to compare same with the server time.

20. A system for data transfer between a server and a respirator, wherein the respirator comprises a source for breathing gas, at least one interface to enable a data transfer, a device for determining data, a control unit, a memory, and a timer unit for specifying a system time, wherein the respirator is configured to give the data a timestamp, to store the data and to transfer the data at a later point in time, wherein the timestamp is designed so that it cannot be adjusted, or can only be adjusted to a limited extent to a tolerance window, wherein the system is configured to carry out a comparison of a system time of the respirator with a server time of the server on the basis of the timestamp when the data transfer is started, and wherein the respirator comprises a display time that is designed to differentiate itself from the system time by up to 24 hours.

\* \* \* \* \*